United States Patent [19]

Rossi

[11] Patent Number: 4,967,754
[45] Date of Patent: Nov. 6, 1990

[54] METHOD AND APPARATUS FOR ANTICIPATING SIDE EFFECTS MANIFESTED IN A PATIENT DURING DIALYSIS TREATMENT

[75] Inventor: Marco Rossi, Medolla, Italy
[73] Assignee: Hospal AG, Basel, Switzerland
[21] Appl. No.: 364,292
[22] Filed: Jun. 12, 1989

[30] Foreign Application Priority Data

Jun. 15, 1988 [IT] Italy ................. 67564 A/88

[51] Int. Cl.$^5$ ............................................. A61B 5/02
[52] U.S. Cl. ................................. 128/670; 604/5
[58] Field of Search ............... 128/668, 670–671, 128/630, 389, 700; 604/4–6, 29

[56] References Cited

U.S. PATENT DOCUMENTS

| | | | |
|---|---|---|---|
| 3,814,082 | 6/1974 | Taylor | 128/670 |
| 4,098,274 | 7/1978 | Ebling et al. | 604/5 |
| 4,473,081 | 9/1984 | Dioguardi et al. | 128/670 |

*Primary Examiner*—Max Hindenburg
*Attorney, Agent, or Firm*—Finnegan, Henderson Farabow, Garrett & Dunner

[57] ABSTRACT

An apparatus and method for anticipating side effects which are manifested in a patient during a dialysis treatment, respectively comprising a device and step for measuring at least one haemodynamic value of the patient a predetermined number of times to obtain a parameter corresponding to the variation of the haemodynamic value with respect to time, a device and step for calculating a rating corresponding to a mean variation of the parameter with reference to a predetermined period, a device and step for comparing the value of the rating with a reference value delimiting a range of safety values, and a device and step for emitting an alarm signal each time the value of the rating falls outside the range of safety values delimited by the reference value.

13 Claims, 3 Drawing Sheets

METHOD AND APPARATUS FOR ANTICIPATING SIDE EFFECTS MANIFESTED IN A PATIENT DURING DIALYSIS TREATMENT

BACKGROUND OF THE INVENTION

1. Field of the Invention

The present invention relates to a method and an apparatus for anticipating side effects manifested in a patent undergoing a dialysis treatment. More precisely, the present invention relates to a method and an apparatus for monitoring and detecting early indications of the manifestation of undesirable side effects such as, for example, nausea, vomiting, hypotension, headaches and above all, collapse.

2. Description of the Related Art

Currently, there are three fundamental intervention procedures for avoiding adverse side effects during dialysis treatment. According to a first procedure, an operator or a nurse takes periodic measurements (every half hour, every hour) of the arterial pressure, cardiac rate and, in certain cases, weight loss. This monitoring is discontinuous and intermittent and the responsibility for the monitoring is entrusted exclusively to the operator who intervenes according to visual assessments of the patient's condition and the patient's own suggestion. It is obvious that this procedure does not allow for immediate corrective interventions necessary to prevent any malaise in the patient which frequently appears quite suddenly.

A second control procedure utilizes knowledge of the physiological dialysis process to adjust the dialysis machine to allow it to perform treatments with the least possible disturbance effect. The results are distinctly better than those obtained according to the first intervention procedure referred to above. However, it has not yet been possible to prevent the manifestation of collapse (certainly the most characteristic and one of the most serious side effects) precisely because certain machines are programmed to bring certain treatment parameters as close as possible to those which have been considered to be most adequate (on a theoretical basis) for the patent undergoing dialysis, without utilizing signals coming from the patient himself. Possible corrective and/or preventive interventions are, in certain cases, even left to the operator's discretion.

A third control procedure takes into account specific signals ascertained in the patient. Such a procedure is the subject of research in the field of dialysis and has not yet given rise to satisfactory concrete embodiments, either because of the difficulties in identifying and measuring certain fundamental physical characteristics of the patient or because of difficulty in defining an efficient strategy for processing and utilizing signals corresponding to the above-mentioned characteristics. The present invention effectively overcomes this difficulty.

An object of the present invention is to provide a method and apparatus capable of anticipating, with a good level of reliability, the appearance of side effects manifesting themselves in a patient undergoing a dialysis treatment, allowing an operator to intervene in good time and/or to automatically activate a procedure preventing the appearance of such effects.

SUMMARY OF THE INVENTION

To achieve the foregoing objects, and in accordance with the purposes of the invention as embodied and broadly described herein, there is provided a method for anticipating side effects which manifest themselves in a patient during a dialysis treatment. This method is characterized by the sequence of the following operations: (1) measuring at least one of the patient's haemodynamic values to obtain at least one parameter corresponding to the variation of this value with respect to time; (2) utilizing this parameter to obtain at least one rating corresponding to a variation of this parameter with reference to a predetermined period; (3) comparing the value obtained for the rating with at least one reference value delimiting a range of safety values; and (4) emitting an alarm signal which can be used as a control signal each time the value obtained for the said rating departs from the range of safety values delimited by the said reference value.

The objects of the present invention are also achieved with the apparatus for anticipating side effects manifesting themselves in a patient during a dialysis treatment. This apparatus comprises means for measuring at least one of the patient's haemodynamic values capable of providing at least one parameter corresponding to the variation of the value with respect to time, means for calculating at least one rating corresponding to a mean variation of this parameter with reference to a predetermined period, means for comparing the value obtained for the rating with at least one reference value delimiting a range of safety values, and means for emitting an alarm signal which can be used as a control signal each time the value obtained for the rating departs from the range of safety values delimited by the reference value.

To render the present invention more readily understood, a preferred mode of embodiment will be described below purely by way of a non-restrictive example and with reference to the attached drawings.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

DESCRIPTION OF THE PREFERRED EMBODIMENTS

Figure 1:
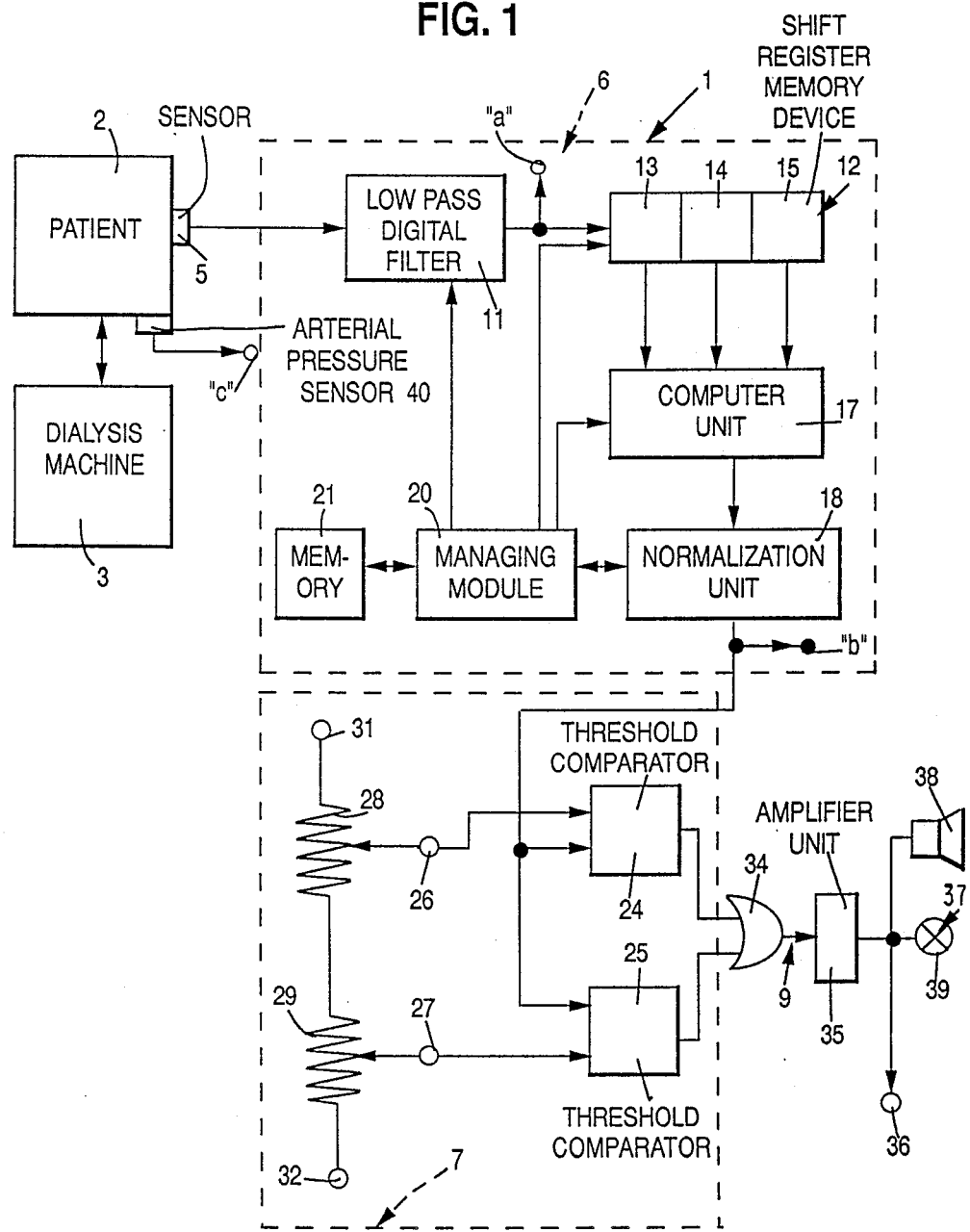
FIG. 1 is a schematic diagram of an apparatus according to the present invention.

Reference will now be made in detail to the present preferred embodiments of the invention as illustrated in the accompanying drawings. In accordance with the present invention and as depicted in FIG. 1, there is provided an apparatus for anticipating side effects which can manifest themselves in a patient 2 during a dialysis treatment with a known dialysis machine 3.

According to the present invention, the apparatus 1 essentially comprises a sensor 5 capable of measuring a haemodynamic value of the patient, and of supplying a signal parameter corresponding to the variation of the haemodynamic value itself with respect to time.

The signal generated by sensor 5 is sent to unit 6 for processing. Unit 6 calculates at least one rating corresponding to a variation of the above-mentioned parameter with reference to a predetermined period, and circuit 7 compares the value obtained for the above-mentioned rating with at least one reference value delimiting a predetermined range of safety values. A circuit 9 emits an alarm signal which can be used as a control signal each time the value obtained for the rating calculated by unit 6 exceeds the range of safety values delimited by the above-mentioned reference value.

The detailed description that follows uses the cardiac rate as an example of the haemodynamic value measured.

In view of the preceding considerations, the sensor 5 can, for example, be a simple frequency meter, one of whose outputs is connected to a low pass digital filter 11 forming part of the processing unit 6. The essential function of filter 11 is to eliminate noise. Filter 11 lets only the physiological signals pass which are emitted by the sensor 5 in their own frequency range.

Processor unit 6 also comprises a shift register memory device 12 having multiple memory cells. In a preferred embodiment, memory device 12 comprises, for example, three identical cells 13, 14, 15, wherein the first cell 13 is connected to the output of the filter 11. Each cell stores a separate haemodynamic value for different points in time.

Unit 6 further comprises a computer unit 17 provided with three signal inputs respectively connected to the parallel outputs of the cells 13, 14, 15 of the memory device 12. A normalization unit 18 is also provided, having an input connected to the output of the unit 17 and an output connected to an input of the comparison circuit 7.

The computer unit 17 is, for example, capable of performing a least square linear regression operation in order to compute the "ai" and "bi" coefficients or the slopes of the line segments obtained (see FIG. 3a), defined by the three values stored in memory cells 13, 14, and 15 with respect to the y axis.

The sole object of the normalization unit 18 is to calculate for the "ai" slope of each line segment, a corresponding value "a'i" between $-1$ and $+1$, by applying, for example, the following formula:

$$a'i = \frac{ai}{\sqrt{i + ai^2}}$$

Unit 6 is also provided with a managing module 20, comprising, for example, a microprocessor which is connected to a memory 21 and to all the above-mentioned components (filter 11, memory device 12, computer unit 17 and normalization unit 18), for coordinating the transmission of the signals between the components. In fact, all of unit 6 can be advantageously constituted by a microprocessor.

The comparison circuit 7 may be of the conventional type wherein it includes a pair of threshold comparators 24, 25, each having a first input connected to the output of the unit 6. In this particular case, for example, the normalization unit 18 and a second input are respectively connected by a sliding contact 26, 27 to a potentiometer 28, 29.

The potentiometers 28, 29 are connected in series and have their respective opposite terminals connected to the terminals 31, 32. A direct current supply (not shown) is attached to terminals 31 and 32, terminal 31 being positive and terminal 32 being negative.

The comparators 24, 25 are provided so that their threshold signals at their respective output remain at the "0" logic level until the first input signal from unit 6 is between the values of the reference voltage on the sliding contacts 26, 27. The output signals pass to the "1" logic level each time the signal present at the first input is either higher or lower than the above-mentioned corresponding reference values.

Circuit 9, which emits an alarm signal that can be used as a control signal, may be an OR type logic gate 34 with two inputs respectively connected up-line to the outputs of the comparators 24, 25, and with an output connected down-line to an amplifier unit 35.

The output of the amplifier unit 35 is connected to a terminal 36 as well as to alarm means 37 that may include a sound alarm 38 and a lamp 39.

Figure 2A:
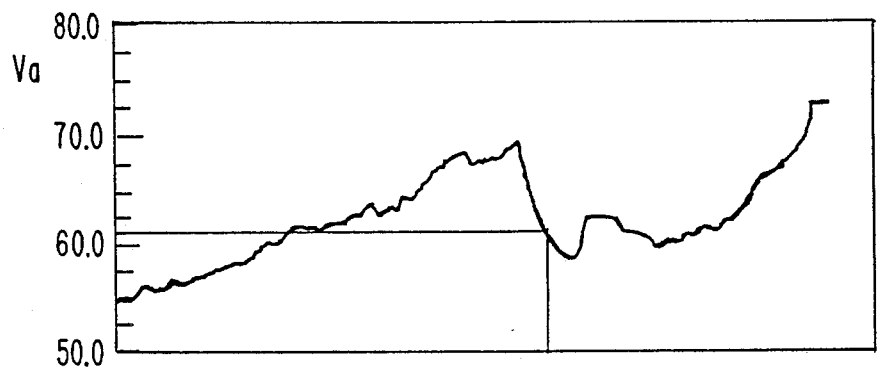
FIG. 2 is a series of graphs depicting an example of signals taken in succession at points a, b, and c of the diagram of FIG. 1 in a specific clinical case, FIG. 2a showing the course, with respect to time, of the cardiac rate after filtration.
FIG. 2b showing the corresponding values for the "ai" slopes of successive line segments, calculated by the normalization unit between $-1$ and $+1$ of the cardiac rate.
FIG. 2c showing the mean arterial pressure.
Figure 2B:
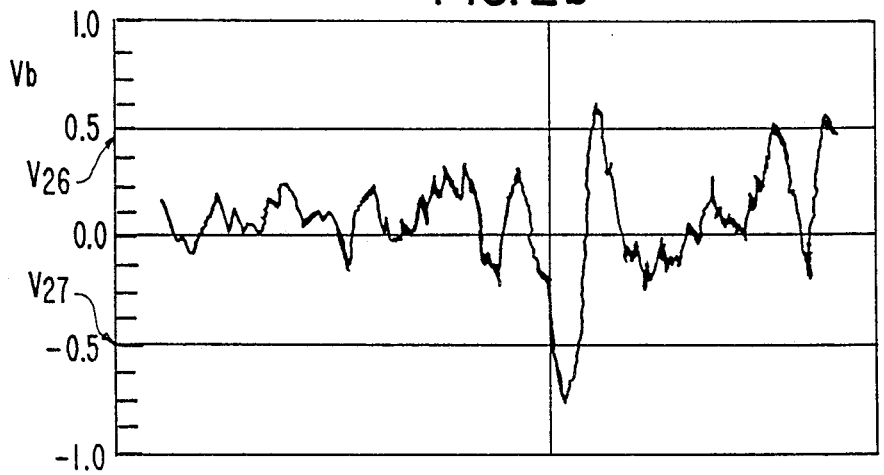
Figure 2C:
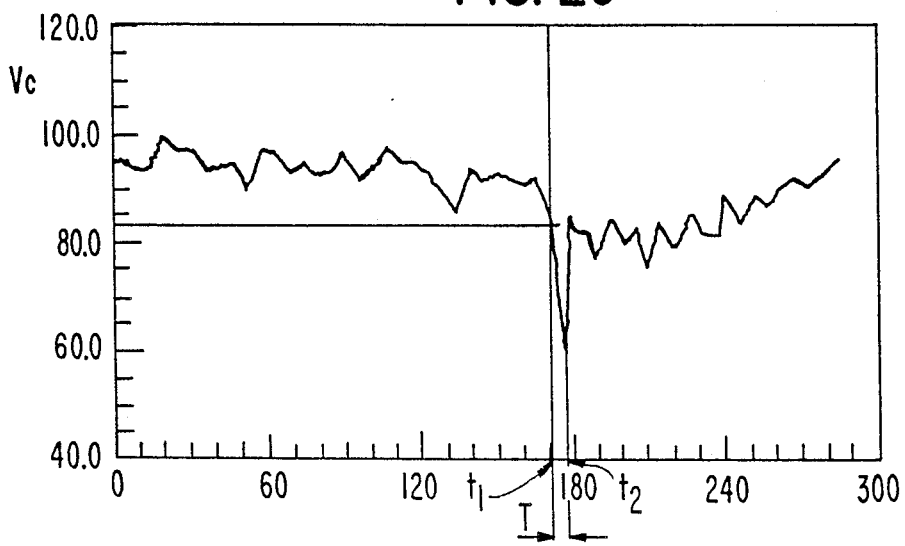

The output of the low pass filter 11 is also connected to terminal "a", and the output of the normalization unit is connected to terminal "b". Moreover, a patient 2 is connected to an arterial pressure sensor 40, an output of which passes to terminal "c". FIGS. 2a, 2b, 2c, illustrate the electrical signals measured at the above-mentioned terminals "a", "b", "c", on a time base expressed in minutes, and are respectively indicated as Va, Vb, Vc. In FIG. 2b, V26 and V27 represent the two corresponding values of the respective threshold voltages measured pari passu by the sliding contacts 26, 27 of the potentiometers 28, 29.

Figure 3A:
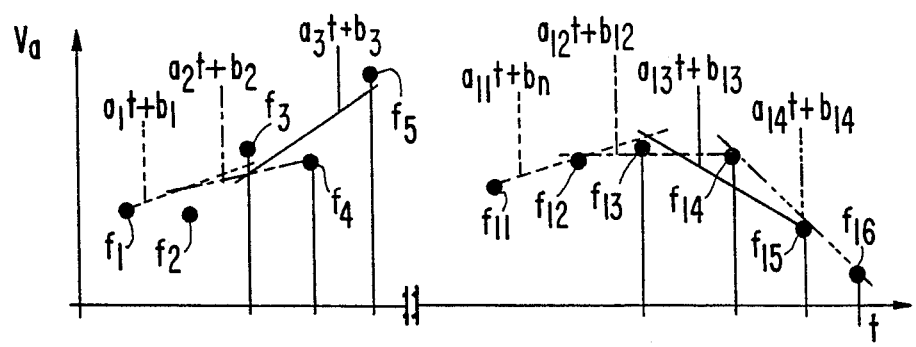
FIG. 3 is a series of graphs illustrating representations of the processing of the signals carried out by the apparatus of FIG. 1.
Figure 3B:
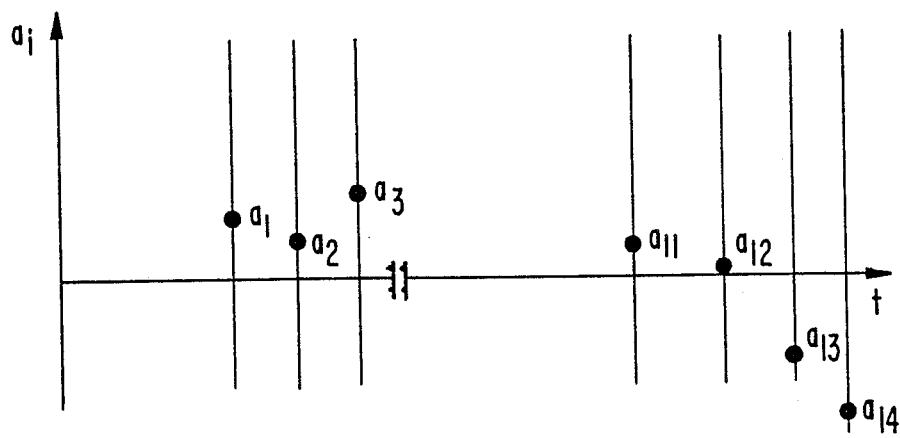
Figure 3C:
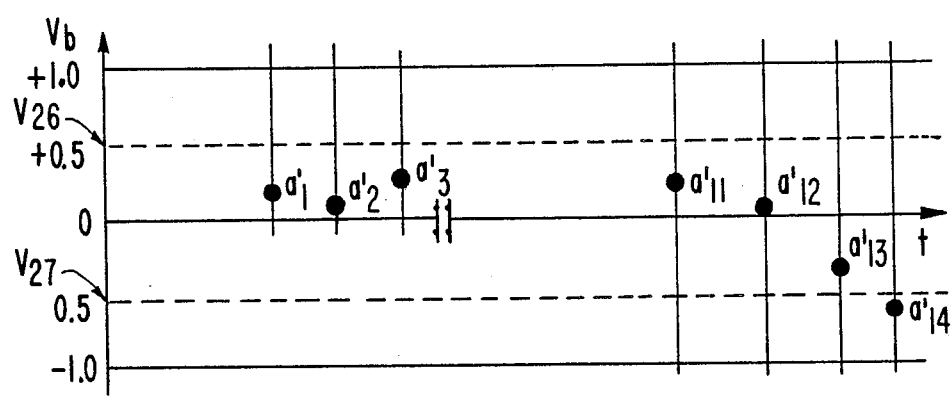

FIG. 3 graphically illustrates two examples of the mathematical processing of signal Va (FIG. 3a) so as to initially obtain a plurality of ai coefficients (FIG. 3b) corresponding to the slopes of the lines segments obtained by linear regression in accordance with the above-mentioned procedures. FIG. 3c illustrates a normalization between $-1$ and $+1$ of the values obtained from coefficients of FIG. 3a.

The following successive operations occur in the method of the present invention: (1) measuring the cardiac rate of the patient; (2) calculating at least one rating correlative to the variation of the frequency with reference to a predetermined period; (3) comparing the rating with at least one reference value delimiting a range of safety values; and (4) emitting an alarm signal which can be utilized as a control signal, each time the rating value moves outside the limits of the range of safety values delimited by the reference value.

In greater detail, the signal proportional to the cardiac rate is measured by sensor 5, filtered by low pass filter 11, and stored in groups of three values in the graduated memory device 12. For example, the first three measured frequency values f1, f2, f3 (see FIG. 3a) are respectively stored in the cells 15, 14, 13 of the memory device 12. The next measured value f4 occupies cell 13 and displaces the f3 and f2 values into the cells 15 and 14 excluding the f1 value, and so on. For each group of three frequency values stored in the memory device 12, the computer unit 17 calculates a linear regression in accordance with the above specifications to determine the "ai" and "bi" coefficients of the corresponding line obtained. The calculations take into account f1, f2, f3, "a2" and "b2" as well as f2, f3, f4 and so on. In this way, a sequence of the "ai" values is obtained (see FIG. 3b) which are measured at the output of the computer unit 17 and which represent, as a whole, the slope of the cardiac rate signal measured by sensor 5 and filtered by filter 11.

The normalization unit 18 regulates the noted "ai" values to obtain the corresponding "a'i" values with an amplitude between $-1$ and $+1$, as specified above.

The next step consists of a comparison to determine whether each one of the "a'i" values lies within a range of safety values, delimited at the top and bottom by the two respective threshold values V26 and V27. This operation is accomplished by the comparison circuit 7 by means of the comparators 24, 25 and the potentiometers 28 and 29. In the event one of the "ai" values falls outside the established limits (see, for example, the value "a'14" of FIG. 3c), the comparator 24 or 25 sends a logic level "1" signal to the corresponding input of OR gate 34. This results in the switching of the respective logic output signal from "0" to "1" and the consecutive emission of a control signal by amplifier unit 35. Amplifier unit 35 triggers the operation of sound alarm 38 and lamp 39, and sends an electric signal to terminal 36 which can be utilized for subsequent use, for example, for automatically modifying certain parameters of the dialysis effected by dialysis machine 3.

FIG. 2 relates to an actual case wherein the "cardiac rate" haemodynamic value is measured every ten heartbeats and is filtered by a digital band pass filter of the conventional type. The alarm rating constituted by "the normalized slope," is obtained by a linear regression over 15 samples (in this case, the shifting register 12 would have to include 15 cells.) Observing this figure in detail, it will be seen that the output of the signal Vb beyond the lower safety threshold V27 is produced at time t1, followed by a time interval T (approximately 7 minutes). Time t2 corresponds to a point where the patient's mean arterial pressure undergoes a sudden drop, producing a cardio-circulatory collapse. In actual cases, like the one depicted in FIG. 2, the importance of anticipating sudden biological changes such as the one described above is clearly established. In fact, the detection of an irregularity occurs at time t1, while the effective values of the cardiac rate (approximately 61 beats/minute) and the mean arterial pressure (approximately 83 mm Hg) can still be considered to be fully within the norm for the type of patient undergoing dialysis. This shows that the analysis of the instantaneous data provided by the instruments capable of measuring these values proves to be inadequate for purpose which the present invention aims to attain.

The following obvious advantages become apparent upon examining the characteristics of the method and the apparatus of the present invention. Primarily, it is possible to obtain an early indication of a critical physiological situation. This allows counter measures to be taken in time to prevent the patient from having a cardio-circulatory collapse, with all the negative consequences that such a situation would entail. This is especially useful for patients with heart disease. By utilizing the data supplied by the apparatus in time, the technician can provide for an automatic, opportune, and efficient intervention. For example, the operator can make adjustments to the dialysis procedure by varying the dialysis machine 3.

Finally, it is clear that modifications and variants may be introduced to the method and the apparatus described above without departing from the scope of the present invention. Above all, the analysis of the signal can be far more complex if a set of ratings is created, wherein each has to be compared with at least one corresponding threshold. More simply, the number of regression samples, and corresponding number of cells of the shifting register memory device, could vary either from one session to another, or dynamically in accordance with the characteristics of the signal. Moreover, even if the cardiac rate is the chosen value to be measured, other haemodynamic values can also be measured so that one, or several parameters (amplitude, frequency, etc.) can be considered, being related to this haemodynamic value with respect to time. By way of example, measurements and calculations could be undertaken on the cardiac amplitude signal and on the electrocardiograph signal by suitably using a non-invasive cardiac amplitude measurement device and a conventional electrocardiograph monitor.

Additional advantages and modifications will readily occur to those skilled in the art. The invention in its broader aspects is, therefore, not limited to the specific details, representative apparatus, and illustrative examples shown and described. Accordingly, departures may be made from such details without departing from the spirit or scope of the general inventive concept as defined by the appended claims and their equivalents.

What is claimed is:

1. A method for anticipating side effects capable of manifesting themselves in a patient during a dialysis treatment, comprising the steps of:

measuring at least one haemodynamic value of the patient a predetermined number of times to establish a general trend with respect to time of said at least one haemodynamic value;

calculating, using linear regression analysis, at least one rating corresponding to the slope of a line segment following said general trend;

comparing said at least one rating with at least one reference value delimiting a range of predetermined safety values; and emitting an alarm signal each time said at least one rating falls outside of said range of safety values.

2. A method according to claim 1, wherein said at least one measured haemodynamic value is chosen from the group consisting of the following values: cardiac rate, electrocardiograph signal, and cardiac amplitude.

3. A method according to claim 1, further comprising the step of regulating dialysis treatment in response to an alarm signal emission.

4. An apparatus for anticipating side effects which are manifested in a patient during a dialysis treatment, comprising:

means for measuring at least one haemodynamic value of the patient a predetermined number of times to establish a general trend with respect to time of said at least one haemodynamic value;

means for calculating, using linear regression analysis, at least one rating corresponding to the slope of a line segment following said general trend;

means for comparing the value of said at least one rating with at least one reference value delimiting a range of safety values; and means for emitting an alarm signal each time the value of said rating falls outside the range of safety values delimited by said at least one reference value.

5. An apparatus according to claim 4, wherein the measurement means measures a haemodynamic value chosen from the group consisting of the following: cardiac rate, electrocardiograph signals, and cardiac amplitude.

6. An apparatus according to claim 4, wherein said calculating means includes a filter disposed down-line from said measurement means.

7. An apparatus as set forth in claim 4, wherein said calculating means includes memory means for storing said predetermined number of haemodynamic values supplied by said measurement means, and rating means for calculating said rating.

8. An apparatus as set forth in claim 4, wherein said calculating means further comprises a microprocessor.

9. An apparatus as set forth in claim 4, wherein said comparison means comprises at least one threshold comparator.

10. An apparatus as set forth in claim 9, wherein said comparison means further comprises at least one element for regulating a threshold reference value of the threshold comparator.

11. An apparatus as set forth in claim 4, wherein said means emits an acoustic signal.

12. An apparatus as set forth in claim 4, wherein said means emits an optical signal.

13. An apparatus as set forth in claim 4, further comprising means for controlling a dialysis machine in response to said emission of said alarm signal.

* * * * *

UNITED STATES PATENT AND TRADEMARK OFFICE
CERTIFICATE OF CORRECTION

PATENT NO. : 4,967,754

DATED : November 6, 1990

INVENTOR(S) : Rossi

It is certified that error appears in the above-identified patent and that said Letters Patent is hereby corrected as shown below:

Claim 11, column 8, line 9, before "means", insert --emitting--.

Claim 12, column 8, line 11, before "means" insert --emitting--.

Signed and Sealed this

Twenty-fifth Day of February, 1992

Attest:

HARRY F. MANBECK, JR.

*Attesting Officer*     *Commissioner of Patents and Trademarks*